United States Patent [19]

Miyazaki et al.

[11] 4,139,610

[45] Feb. 13, 1979

[54] PERMANENT WAVING COMPOSITION

[75] Inventors: Yoshimasa Miyazaki, Hirakata; Shigeru Matsumura, Kashiwa; Takayoshi Yamauchi, Sakai; Morio Harada, Nishinomiya; Hisatoshi Shimizu, Sakai, all of Japan

[73] Assignee: Kyowa Hakko Kogyo Kabushiki Kaisha, Tokyo, Japan

[21] Appl. No.: 787,409

[22] Filed: Apr. 14, 1977

[30] Foreign Application Priority Data

Apr. 19, 1976 [JP] Japan ................................ 51-43609

[51] Int. Cl.$^2$ .......................... A61K 7/09; A45D 7/04
[52] U.S. Cl. ........................................ 424/72; 424/71; 132/7
[58] Field of Search .................. 424/70, 71, 72; 132/7

[56] References Cited

U.S. PATENT DOCUMENTS

| | | | |
|---|---|---|---|
| 1,608,686 | 11/1926 | Weil | 424/70 |
| 2,717,228 | 9/1955 | Brown | 424/71 |
| 3,109,777 | 11/1963 | Zviak | 132/7 |
| 3,242,052 | 3/1966 | Sheffner | 132/7 |

FOREIGN PATENT DOCUMENTS 1187568  4/1970  United Kingdom ................. 132/7 X

OTHER PUBLICATIONS

Chemical Abstracts vol. 50:2550f & vol. 69:941g.

*Primary Examiner*—Donald B. Moyer
*Attorney, Agent, or Firm*—Wolder, Gross & Yavner

[57] ABSTRACT

Permanent waving composition containing as active ingredients cysteine and N-acetylcysteine. The composition contains preferably 3–15% cysteine and 0.2–3% N-acetylcysteine. It is possible to avoid the separation of crystals derived from the air-oxidation of cysteine by the composition of the present invention.

7 Claims, No Drawings

PERMANENT WAVING COMPOSITION

The present invention relates to permanent waving composition. Permanent waving compositions containing thioglycollic acid were previously known. However, the activity of thioglycollic acid on the hair of human is strong so that the permanent waving compositions of this type can give rise to the allergic reactions on the skin, damage to the hair roots, the breaking, falling and discolouring of the hair and other undesired side effects. Recently, permanent waving compositions containing cysteine as active ingredient have been proposed. Although cysteine possesses a milder activity on the hair when compared with the activity of thioglycollic acid, the stability of cysteine is more or less doubtful. For example, when applied to the hair of users, the crystals derived from cysteine are liable to be separated from the permanent waving compositions onto the hair and skin owing to the air-oxidation, which results in the lowering of operational efficiency and also damage to the skin of the user and artist. Another defect of cysteine resides in a poor storage stability.

Various proposals have been made to overcome the above-mentioned difficulties. For example, Japanese PS No. 14934/73 discloses a permanent waving composition for the socalled cold permanent waving system, which contains cysteine as active ingredient in an amount of 3–15% by weight and has a pH of from 7 to 10. The storage stability is improved by addition of thioglycollic acid in an amount which is as itself inoperative in permanent waving, together with ethylenediamine tetraacetic acid, nitrilotriacetic acid or water-soluble salts thereof. Japanese PS No. 48504/74 discloses a permanent waving composition for the cold permanent waving system containing as active ingredients both L- and D-cysteine at a ratio of 7:3 to 3:7 by weight and having pH of 7–12, whereby to avoid the separation of the crystals derived from air-oxidized L-cysteine. However, the results of experiments conducted by us revealed that these processes were insufficient to inhibit the separation of the crystals when applied to the hair of human. On the other hand, a permanent waving composition containing as active ingredient N-alkanoylcysteine such as N-acetylcysteine in an amount of 3–20% (preferably 7–10%) by weight exhibits an excellent stability and safety of the hair (U.S. Pat. No. 3,242,052). However, permanent waving composition of this type has the disadvantage that the composition is very slippery on the hands of the artist and the operational efficiency is considerably lowered when applied to the hair tightly rolled. In addition, the composition of this type is expensive because N-acetylcysteine is derived from cysteine.

It has unexpectedly been discovered that permanent waving composition containing as active ingredients both cysteine and N-acetylcysteine exhibits improved properties without the above-mentioned defects.

An object of the present invention is to provide a permanent waving composition without the above-mentioned defects, which may be produced at cheaper costs and which may be used for both the cold system and the heat system with excellent results.

According to the present invention, there is provided a permanent waving composition, which comprises cysteine and and N-acetylcysteine as active ingredients.

Permanent waving compositions of the known types contain usually cysteine in an amount of about 3–15% cystein [% denotes % (weight/volume) hereinafter otherwise specified] when cysteine is used as active ingredient. In a preferred embodiment of the present invention, the composition contains cysteine in an amount of about 3–15% and N-acetylcysteine in an amount of about 0.2–3% of the composition to inhibit the separation of the crystals derived from cystein. On the other hand, the presence of N-acetylcysteine solely in an amount of not more than 3% is inoperative in permanent waving, as is previously known.

Advantageously, the higher the amount of cysteine is, the more the absolute amount of N-acetylcysteine is. It is usually preferred to use N-acetylcysteine amounting to more than about 10% by weight of cysteine present in the composition according to the present invention. However, when the amount of cysteine rises to more than about 10%, it is then advantageous to use N-acetylcysteine in an amount of more than about 30% by weight of cysteine. In general, the presence of more than about 10% of cysteine and more than about 3% of the composition seems to be superfluous for practical use because the presence of more than about 3% of the composition of N-acetylcysteine is not only liable to cause the above-mentioned slipping trouble in use but also expensive without additional merit.

Especially good results may be obtained when the amount of cysteine and N-acetylcysteine contained in the composition according to the present invention is about 4–10% in total.

The pH of the composition in use is adjusted to 7.0–10.0 (preferably about 7.2 when used for the cold permanent waving). For this purpose, it is conventional to use for example ammonia, ethylenediamine, ethanolamine, diethanolamine, triethanolamine, piepridine, caustic soda and like. It is also conventional to add to the composition a suitable chelating agent (e.g. ethylenediamine tetraacetic acid, nitrilotriacetic acid, sodium gluconate, sodium tripolyphosphate ans like as a buffer. If desired, it is also possible to add suitable wetting agents (e.g. cetylalcohol), emulsifiers (e.g. glycerine, polyethylene glycol, higher alcohol esters, higher fatty acid esters and like), effect-promoting agents (e.g. urea), thickners, hair nutrients, colouring agents, perfumes and like in convnetional manner. The permanent waving composition according to the present invention may be used for the cold permanent waving and heat permanent waving in conventional manner. The pH of the composition may be adjusted, depending upon the types and purposes of the operations.

Cysteine and N-acetylcysteine used for the present invention may be selected from the free L-, D-, DL-forms and a mixture thereof, although it is also possible to use inorganic salts thereof.

When the composition according to the present invention is preserved in a bottle, it is advantageous to substitute the air in the bottle with nitrogen gas. In this case, the storage stability is at least equal to the storage stabilities of the permanent waving compositions of the known types.

Particular advantages achieved according to the present invention are exemplified as follows. It is possible to avoid the separation of the crystals derived from cysteine on the skin and hair, which is liable to cause various undesired side effects such as allergic reactions. On the other hand, conventional permanent waving composition containing N-acetylcysteine as active ingredient has the inherent disadvantage that the hair applied with the composition is considerably slippery and can hardly held tightly by the hands of artist, resulting in the lowering of operational efficiency. Although the composition according to the present invention also contains N-acetylcysteine, the amount thereof is so small and thus it is possible to avoid the slipping trouble completely. D-cysteine contained in the composition of the known type is derived from L-cysteine and also N-acetylcysteine is derived from cysteine, and the costs thereof are expensive. According to the present invention, it is not necessary to use both L-cysteine and D-cysteine at a certain ratio and the amount of N-acetylcysteine is small, which make the cost cheaper.

The following example including comparative data illustrates the invention.

EXAMPLE (A) Preparation of test samples:

Each sample shown in Table 1 was prepared in the following manner. Cysteine and N-acetylcysteine were dissolved in pure water (20 ml) at room temperature in nitrogen atmosphere. Each solution was adjusted to a pH of 7.0 with addition of ammonia and was then added with sodium ethylenediamine tetraacetic acid (0.05 g) as a buffer. By adding pure water, the solution was made up to 100 ml, and the pH was adjusted to 9.2 (for the cold system) with addition of monoethanolamine. The samples prepared in this manner are shown in Table 1 and may be divided into the following groups: (i) (A) + (B) = 7.0 g; (ii) (A) = 7.0 g and (iii) comparative samples. This was because the examples described in the prior art literatures referred to above use various permanent waving compositions containing active ingredients at a concentration around 7% which may accordingly be deemed as a middle value of practically used concentrations.

TABLE 1

| Sample No. | (A) Cysteine L- | (A) Cysteine D- | (B) N-acetyl cysteine | B/A (%) | (A) + (B) |
|---|---|---|---|---|---|
| 1 | 10.0 | — | — | — | — |
| 2 | 10.0 | — | 3.0 | 30.0 | 13.0 |
| 3 | 7.0 | — | — | — | — |
| 4 | 3.5 | 3.5 | — | — | — |
| 5 | 6.8 | — | 0.2 | 2.9 | 7.0 |
| 6 | 6.65 | — | 0.35 | 5.2 | 7.0 |
| 7 | 6.3 | — | 0.7 | 11.1 | 7.0 |
| 8 | 3.15 | 3.15 | 0.7 | 11.1 | 7.0 |
| 9 | 5.6 | — | 1.4 | 25.0 | 7.0 |
| 10 | 5.38 | — | 1.62 | 30.0 | 7.0 |
| 11 | 4.9 | — | 2.1 | 42.0 | 7.0 |
| 12 | 4.2 | — | 2.8 | 66.7 | 7.0 |
| 13 | 3.5 | — | 3.5 | 100.0 | 7.0 |
| 14 | 3.15 | — | 3.85 | 122.0 | 7.0 |
| 15 | 7.0 | — | 7.0 | 100.0 | 14.0 |
| 16 | 7.0 | — | 4.0 | 57.0 | 11.0 |
| 17 | 7.0 | — | 3.0 | 42.0 | 10.0 |
| 18 | 7.0 | — | 1.75 | 25.0 | 8.75 |
| 19 | 7.0 | — | 0.78 | 11.1 | 7.78 |
| 20 | 7.0 | — | 0.37 | 5.3 | 7.37 |
| 21 | — | — | 3.0 | — | — |
| 22 | — | — | 1.5 | — | — |
| 23 | 3.6 | — | 2.4 | 66.7 | 7.0 |
| 24 | 3.5 | — | 1.5 | 42.9 | 5.0 |
| 25 | 2.1 | — | 0.9 | 42.8 | 3.0 |
| 26 | 7.0 | — | 0.7** | — | — |

**thioglycollic acid (B) Test on the separation of the crystals on the skin:

Each sample (0.5 ml) was dropwise applied to the crotches between the fingers of the left and right hands (each 2 crotches at each hand) of each person of a test panel consisting of 20 persons. The test sample was applied to the same positions daily 4 times i.e. at 9, 11, 13 and 15 o'clock and the hands were allowed to stand without any after-treatment except being washed with water and soap at 12 and 17 o'clock every day. The test samples were prepared every day newly. The same procedures were repeated for one week to observe the changes occured at the crotches. When it was found that a specific sample was liable to cause a heavy allergic effect in the course of the test, then the test was no longer continued. The results are as follows.

No. 1

White crystals were found at the crotches between the fingers of all persons on the first day and could not removed even when washed with water and soap. The test was discontinued.

No. 2

A slight separation of the crystals was found on 2 persons on the 5th day and on all persons on the 6th day. After this, a remarkable tendency to increase was not found. However, the test was not continued further.

No. 3

An almost similar result to that of No. 1.

No. 4

A similar result to that of No. 1 was found on the 2nd day. The test was not continued further.

Nos. 5 and 6

White crystals were found on 4 persons on the 2nd day and on all persons on the 3rd day. The degree of the separation was lower than the degrees observed in Test Nos. 3 and 4. However the test was not continued further.

No. 7

A slight separation of the crystals was found on 2 persons on the 3rd day and a similar result to that of No. 5 was found on all persons on the 4th day. The test was discontinued.

No. 8

A slight separation of the crystals was found on 3 persons on the 5th day and on all persons on the 6th day. The test was discontinued.

No. 9

An analogous tendnecy to that of No. 8 was found. A slight separation of the crystals was observed on all persons on the 6th day, and after this no remarkable change was observed. The test was completed.

No. 10

A similar tendency to that of No. 9 was observed.

Nos. 11–17 and 21–≈

The separation of the crystals and the occurrence of erythema were not found until the completion of the tests.

No. 18

A similar tendency to that of No. 9 was found.

No. 19

A similar tendency to that of No. 7 was found.

No. 20

A similar tendency to that of No. 6 was found.

No. 26

White crystals were separated on several persons on the first day and on almost all persons on the 2nd day, and the test was discontinued. The result was similar to that in No. 1.

From these results, it has been confirmed that the separation of the crystals is liable to increase according to the increase in the absolute amount of cysteine in the composition and/or the decrease in the ratio of N-acetylcysteine to cysteine (B/A in Table 1) and that the degree of the separation onto the skin is liable to rise according to the increase of the period of time, in which the skin was placed in contact with cysteine.

(C) Test on cold permanent waving

In taking into account of the above-mentioned results, the samples shown in Table 2 were used for cold permanent waving test carried out in a usual manner which was obvious for average artists. Namely, each sample and sodium bromate solution (5%) were respectively used as the first and second solutions for convnetional two step cold permanent waving system. The results were evaluated and shown in Table 2 by using the following remarks.

(A) Waving condition and luster of the hair after the treatment: +++ (very good), ++ (good), + (normal) and ± (poor or no good)

(B) Slipping trouble: + (no trouble), ± (light trouble), — (middle trouble) and —(heavy trouble).

Other results than those shown in Table 2 were at least equal to those obtained from conventional cold permanent waving compositions.

TABLE 2

| Sample No. | B/A (%) | (A) + (B) | Waving condition | Luster | Slipping |
|---|---|---|---|---|---|
| 2 | 30.0 | 13.0 | ++ | +++ | ± |
| 7 | 11.1 | 7.0 | ++ | +++ | + |
| 8 | 11.1 | 7.0 | +++ | +++ | + |
| 9 | 25.0 | 7.0 | +++ | +++ | + |
| 12 | 66.7 | 7.0 | +++ | +++ | + |
| 13 | 100.0 | 7.0 | ++ | +++ | — |
| 14 | 122.0 | 7.0 | ++ | +++ | — — |
| 15 | 100.0 | 14.0 | ++ | +++ | — — |
| 16 | 57.0 | 11.0 | ++ | +++ | — — |
| 17 | 42.0 | 10.0 | +++ | +++ | — — |
| 18 | 25.0 | 8.75 | +++ | +++ | ± |
| 19 | 11.1 | 7.78 | +++ | +++ | + |
| 20 | 5.3 | 7.37 | ++ | +++ | + |
| 21 | — | — | ± | + | — |
| 22 | — | — | ± | + | ± |
| 23 | 66.7 | 7.0 | +++ | +++ | + |
| 24 | 42.0 | 5.0 | ++ | +++ | + |
| 25 | 42.8 | 3.0 | + | ++ | + |

What is claimed is:

1. A permanent waving composition comprising as active ingredients cysteine in an amount of about 3–15 weight % and N-acetylcysteine in an amount of about 0.2–3 weight %.

2. A composition of claim 1, in which the amount of N-acetylcysteine is about 10% by weight of cysteine.

3. A composition of claim 1, in which the pH of the composition is about 7–10.

4. A permanent waving composition comprising as active ingredients cysteine in an amount of about 3–15 weight % and N-acetylcysteine in an amount of 0.3–3 weight % which is more than 10 weight % of cysteine.

5. A composition of claim 4, in which the amount of cysteine and N-acetylcysteine in total is about 4–10 weight %.

6. A permanent waving composition comprising as active ingredients cysteine in an amount of about 3–15 weight % and N-acetylcysteine in an amount of about 0.2–3 weight %, wherein the amount of N-acetylcysteine is about 10% by weight of cysteine.

7. A method of imparting a wave to human hair which comprises contacting said hair with a composition comprising about 3 to 15 weight percent cysteine and about 0.2 to 3 weight percent N-acetylcysteine.

* * * * *